US00PP34518P2

(12) United States Plant Patent
Schoone

(10) Patent No.: US PP34,518 P2
(45) Date of Patent: Aug. 23, 2022

(54) **X *DORITAENOPSIS* PLANT NAMED 'STREET PARADE'**

(50) Latin Name: **x *Doritaenopsis* (*Doritis* x *Phalaenopsis*)**
Varietal Denomination: Street Parade

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/666,121

(22) Filed: Feb. 7, 2022

Related U.S. Application Data

(60) Provisional application No. 63/148,076, filed on Feb. 10, 2021.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Doritaenopsis* plant named 'Street Parade', characterized by its upright plant habit; moderately vigorous growth habit; strong and moderately elongate leaves; freely flowering habit; reddish purple-colored flowers with dark red-colored labellum and white-colored column; and good postproduction longevity.

2 Drawing Sheets

Figure 1:
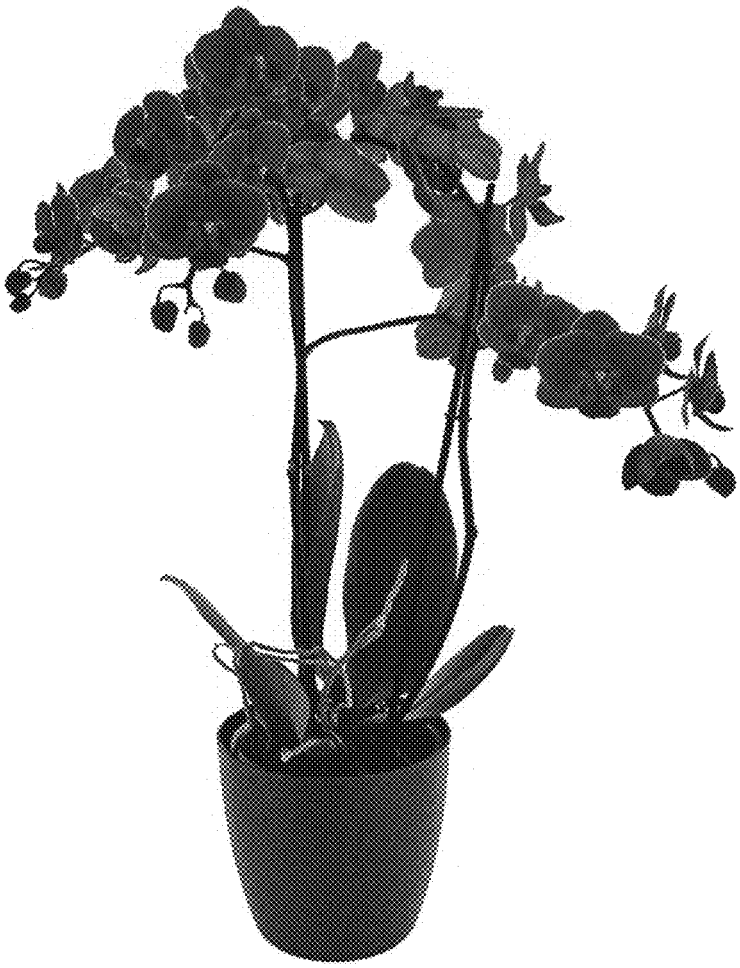

Botanical designation: x *Doritaenopsis* (*Doritis* x *Phalaenopsis*).

Cultivar denomination: 'STREET PARADE'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Mar. 18, 2021, application number 2021/0825. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of x *Doritaenopsis* plant, botanically known as x *Doritaenopsis* (*Doritis* x *Phalaenopsis*), commonly referred to as *Doritaenopsis* and hereinafter referred to by the name 'Street Parade'.

The new *Doritaenopsis* plant is a product of a planned breeding program conducted by the Inventor in Nantou, Taiwan and Heemskerk, The Netherlands. The objective of the breeding program is to develop new fast-growing and freely flowering *Doritaenopsis* plants with good leaf shape and flowers with unique and attractive patterns and coloration.

The new *Doritaenopsis* plant originated from a cross-pollination on Oct.2, 2014 in Nantou, Taiwan of *Doritis hybrida* 'Ching Ann Diamond', not patented, as the female, or seed, parent with *Phalaenopsis hybrida* 'Zuma Pixie', not patented, as the male, or pollen, parent. The new *Doritaenopsis* plant was discovered and selected by the Inventor as a single flowering plant from within the progeny of the stated cross-pollination grown in a controlled greenhouse environment in Heemskerk, The Netherlands in June, 2018.

Asexual reproduction of the new *Doritaenopsis* plant by in vitro meristem propagation in a controlled environment in Assendelft, The Netherlands since June, 2019 has shown that the unique features of this new *Doritaenopsis* plant are stable and reproduced true to type in successive generations.

SUMMARY OF THE INVENTION

Plants of the new *Doritaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Street Parade'. These characteristics in combination distinguish 'Street Parade' as a new and distinct *Doritaenopsis* plant:

1. Upright plant habit.
2. Moderately vigorous growth habit.

3. Strong and moderately elongate leaves.
4. Freely flowering habit.
5. Reddish purple-colored flowers with dark red-colored labellum and white-colored column.
6. Good postproduction longevity.

Plants of the new *Doritaenopsis* can be compared to plants of the female parent, 'Ching Ann Diamond'. Plants of the new *Doritaenopsis* differ primarily from plants of 'Ching Ann Diamond' in flower color as flowers of plants of the new *Doritaenopsis* have fewer stripes than flowers of plants of 'Ching Ann Diamond'. In addition, flowers of plants of the new *Doritaenopsis* do not have any cirrhose apices whereas flowers of plants of 'Ching Ann Diamond' have cirrhose apices.

Plants of the new *Doritaenopsis* can be compared to plants of the male parent, 'Zuma Pixie'. Plants of the new *Doritaenopsis* differ primarily from plants of 'Zuma Pixie' in flower color as flowers of plants of the new *Doritaenopsis* have more stripes than flowers of plants of 'Zuma Pixie'.

Plants of the new *Doritaenopsis* can be compared to plants of *Phalaenopsis hybrida* 'Kissy Lips', disclosed in U.S. Plant Pat. No. 29,337. In side-by-side comparisons, plants of the new *Doritaenopsis* differ primarily from plants of 'Kissy Lips' in flower color as flowers of plants of the new *Doritaenopsis* have more stripes than flowers of plants of 'Kissy Lips'.

BRIEF DESCRIPTION OF THE PHOTOGRAPHS

The accompanying photographs illustrate the overall appearance of the new *Doritaenopsis* plant showing the colors as true as it is reasonably possible to obtain in colored reproductions of this type. Colors in the photographs may differ slightly from the color values cited in the detailed botanical description which accurately describe the colors of the new *Doritaenopsis* plant.

The photograph on the first sheet (FIG. 1) is a side perspective view of a typical flowering plant of 'Street Parade' grown in a container.

Figure 2:
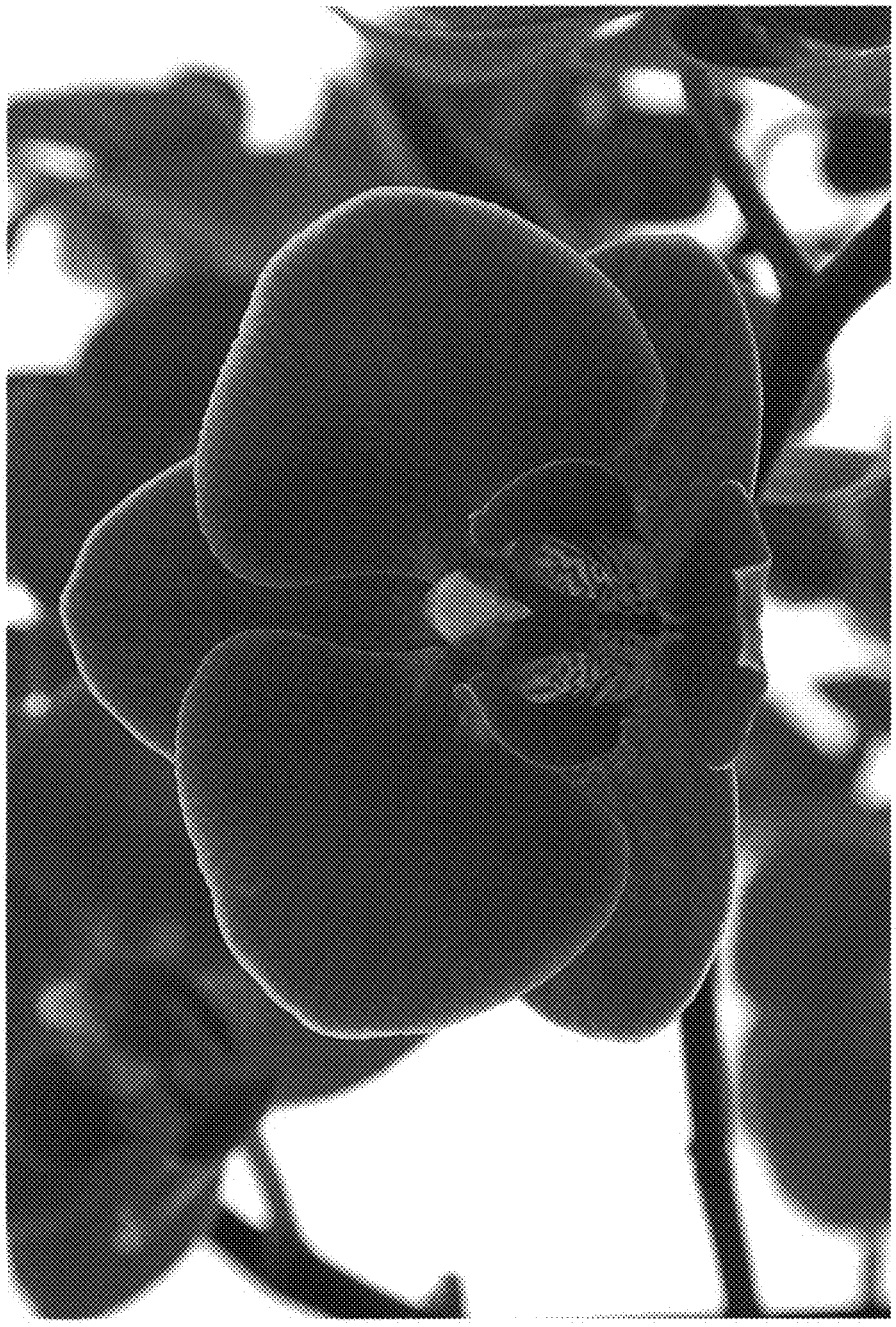

The photograph on the second sheet (FIG. 2) is a close-up view of a typical flower of 'Street Parade'.

DETAILED BOTANICAL DESCRIPTION

The aforementioned photographs and following observations and measurements describe plants grown during the late summer and early autumn in 10.5-cm containers in a glass-covered greenhouse in Heemskerk, The Netherlands and under cultural practices typically used in commercial *Doritaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: x *Doritaenopsis* (*Doritis* x *Phalaenopsis*) 'Street Parade'.

Parentage:

*Female parent.*—*Doritis hybrida* 'Ching Ann Diamond', not patented.

*Male parent.*—*Phalaenopsis hybrida* 'Zuma Pixie', not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Fine, fibrous; typically light yellowish white in color; actual color of the roots is dependent on substrate composition, water quality, fertilizer, substrate temperature and age of roots.

*Rooting habit.*—Freely branching; medium density.

Plant description:

*Plant form and growth habit.*—Herbaceous epiphyte; upright plant habit with typically two inflorescences per plant, each inflorescence with numerous flowers; monopodial; moderately vigorous growth habit and moderate growth rate.

*Plant height, substrate level to top of foliar plane.*—About 14.9 cm.

*Plant height, substrate level to top of inflorescences.*—About 38 cm.

*Plant diameter or spread.*—About 35.8 cm.

Leaf description:

*Arrangement and quantity.*—Distichous, simple; sessile; about five leaves per plant.

*Length.*—About 16.8 cm.

*Width.*—About 7.4 cm.

*Aspect.*—Upright to outwardly arching.

*Shape.*—Oblanceolate; slightly carinate.

*Apex.*—Unequal obtuse.

*Base.*—Sheathing. Sheath length: About 1.7 cm. Sheath width: About 1.3 cm. Sheath color: Close to 143B.

*Margin.*—Entire.

*Texture and luster, upper and lower surfaces.*—Smooth, glabrous; slightly glossy.

*Venation pattern.*—Camptodromous.

*Color.*—Developing leaves, upper surface: Close to NN137B. Developing leaves, lower surface: Close to 147B; margin edges tinged with close to 200B. Fully expanded leaves, upper surface: Close to NN137B; venation, close to NN137A. Fully expanded leaves, lower surface: Close to 146A; margin edges, slightly tinged with close to 200B to 200C; venation, close to 143B.

Inflorescence description:

*Appearance and flowering habit.*—Showy zygomorphic flowers arranged on axillary branched racemes; typically two inflorescences per plant; each inflorescence with about twelve flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about eight weeks on the plant; flowers not persistent.

*Inflorescence length* (*lowermost flower to inflorescence apex*).—About 26.2 cm.

*Inflorescence width.*—About 27 cm.

*Flower buds.*—Height: About 1.7 cm. Diameter: About 1.3 cm by 1.6 cm. Shape: Broadly ovate. Color: Close to 182C; venation, close to N77B.

*Flower size.*—About 4.9 cm (vertical) by 5.5 cm (horizontal).

*Flower depth.*—About 2.5 cm.

*Petals, quantity and arrangement.*—Three, two lateral petals and one center petal transformed into a labellum.

*Lateral petals.*—Length: About 2.8 cm. Width: About 3.2 cm. Shape: Reniform. Apex: Obtuse. Margin: Entire. Texture and luster, upper and lower surfaces: Smooth, glabrous, velvety; matte. Color: When opening, upper surface: Close to a blend of N78A, NN78A and N80A; towards the base, close to a blend of N78A and N79C; narrow margin edges, close to a blend of 76D and N155A; at the base, two small blotches, close to 76C. When opening, lower surface: Close to N80A; center, close to N80C. Fully opened, upper surface: Close to a blend of N78A and NN78A; narrow margin edges, close to a blend of 76D and N155A; at the base, two small blotches, close to 76C; venation, close to NN78A to slightly darker than NN78A. Fully opened, lower surface: Close to N78B; center, close to N80D; venation, close to N78A.

*Labella.*—Appearance: Three-parted with two lateral lobes and a central lobe. Length, lateral lobes: About 1.5 cm. Width, lateral lobes: About 1 cm. Length, central lobe: About 2.8 cm. Width, central lobe: About 0.5 cm to 1.7 cm. Shape, lateral lobes: Obovate. Shape, central lobe: Broadly ovate to roughly rhomboidal. Apex, lateral lobes: Obtuse. Apex, central lobe: Broadly retuse, no cirrhose apices. Margins, lateral and central lobes: Entire. Texture and luster, upper and lower surfaces: Smooth, glabrous, moderately velvety; matte. Callosities: Located at the base of the labellum and attachment point of the lateral petals; about 3 mm in length, about 4 mm in width and about 5 mm in height. Color: When opening and fully opened, upper surface: Lateral lobes: Close to 187B; towards the apex, close to N78A; at the base, close to 155D. Central lobe: Close to 187B; towards the apex, close to N78A; at the base (at column connection), close to 11C with dots, close to 187C. Callosities: Close to 14B with fine dots, close to 187C. When opening and fully opened, lower surface: Lateral lobes: Close to a blend of N78A and N79C; towards the base, close to 156B to 156C. Central lobe: Close to N79C; towards the apex, close to N78B; center, close to 76A; at the base (at column connection), close to 156A to 156B; venation, close to N79C. Callosities: Close to 14C with fine dots, close to 187C.

*Sepals.*—Quantity and arrangement: Three, one upper dorsal sepal and two lower lateral sepals. Length, dorsal sepal: About 2.9 cm. Width, dorsal sepal: About 2.7 cm. Length, lateral sepals: About 2.9 cm. Width, lateral sepals: About 2.4 cm. Shape, dorsal and lateral sepals: Broadly ovate. Apex, dorsal sepal: Obtuse. Apex, lateral sepals: Obtuse to bluntly acute. Base, dorsal and lateral sepals: Truncate. Margin, dorsal and lateral sepals: Entire. Texture and luster, all sepals, upper and lower surfaces: Smooth, glabrous, velvety; matte. Color, dorsal sepal: When opening, upper surface: Close to N78A; center and towards the base, close to N79C; narrow margin edges, close to 76C; venation, darker than NN78A. When opening, lower surface: Close to N78B; center, close to 186D; narrow margin edges, close to 76C; venation, close to N77B. Fully opened, upper surface: Close to N78A; towards the base, close to a blend of N78A and NN78A; narrow margin edges, close to 76C; venation, darker than NN78A. Fully opened, lower surface: Close to N75D; towards the margins and apex, close to N78B; narrow margin edges, close to 76C; venation, close to N78B. Color, lateral sepals: When opening, upper surface: Close to N78A; at the base, fine dots, close to 196B; narrow margin edges, close to 76C; venation, close to N79C. When opening, lower surface: Close to 72B; center, close to 186D; narrow margin edges, close to 76C; venation, close to N78A. Fully opened, upper surface: Close to N78A; towards the base, fine dots, close to 186D; narrow margin edges, close to 76C; venation, slightly darker than a blend of N78A and NN78A. Fully opened, lower surface: Close to N75D; towards the margins and apex, close to 77B; narrow margin edges, close to 76C; venation, close to N78B.

*Peduncles.*—Length: About 48.3 cm. Diameter: About 5 mm. Strength: Strong. Aspect: Upright to outwardly arching. Texture and luster: Smooth, glabrous; matte. Color: Close to 200A densely covered with fine dots, close to 147D.

*Pedicels.*—Length: About 3.1 cm. Diameter: About 2 mm. Strength: Moderately strong. Aspect: About 90° from peduncle axis. Texture and luster: Smooth, glabrous; matte. Color: Close to 197B; distally, close to 70B and proximally, close to 200D tinged with close to N186C.

*Reproductive organs.*—Androecium: Column length: About 8 mm. Column width: About 4 mm. Column color: Close to N78A and NN78A; towards the apex, close to NN155A. Pollinia quantity: Two. Pollinia diameter (per two pollinia): About 2 mm. Pollinia color: Close to 24A. Gynoecium: Stigma length: About 3.5 mm. Stigma width: About 4 mm. Stigma shape: Reniform. Stigma color: Close to 76C. Ovary length: About 9 mm. Ovary diameter: About 1 mm. Ovary color: Close to 147D. Seeds and fruits: To date, seed and fruit development have not been observed on plants of the new *Doritaenopsis*.

Pathogen & pest resistance: To date, plants of the new *Doritaenopsis* have not been shown to be resistant to pathogens and pests common to *Doritaenopsis* plants.

Temperature tolerance: Plants of the new *Doritaenopsis* have been observed to tolerate high temperatures to about 40° C. and are suitable for USDA Hardiness Zones 10 to 12.

It is claimed:

1. A new and distinct *Doritaenopsis* plant named 'Street Parade' as illustrated and described.

* * * * *